US011120897B2

(12) United States Patent
Singh et al.

(10) Patent No.: US 11,120,897 B2
(45) Date of Patent: Sep. 14, 2021

(54) SYSTEM AND METHOD FOR TRACKING INFORMAL OBSERVATIONS ABOUT A CARE RECIPIENT BY CAREGIVERS

(71) Applicant: Lifeline Systems Company, Framingham, MA (US)

(72) Inventors: Portia E. Singh, Everett, MA (US); Mladen Milosevic, Stoneham, MA (US)

(73) Assignee: Lifeline Systems Company, Framingham, MA (US)

( * ) Notice: Subject to any disclaimer, the term of this patent is extended or adjusted under 35 U.S.C. 154(b) by 87 days.

(21) Appl. No.: 16/099,368

(22) PCT Filed: May 11, 2017

(86) PCT No.: PCT/EP2017/061242
§ 371 (c)(1),
(2) Date: Nov. 6, 2018

(87) PCT Pub. No.: WO2017/194642
PCT Pub. Date: Nov. 16, 2017

(65) Prior Publication Data
US 2019/0206533 A1 Jul. 4, 2019

Related U.S. Application Data

(60) Provisional application No. 62/335,972, filed on May 13, 2016.

(51) Int. Cl.
*G16H 10/60* (2018.01)
*G16H 15/00* (2018.01)
(Continued)

(52) U.S. Cl.
CPC .......... *G16H 10/60* (2018.01); *G06Q 10/063* (2013.01); *G16H 15/00* (2018.01); *G16H 40/20* (2018.01);
(Continued)

(58) Field of Classification Search
None
See application file for complete search history.

(56) References Cited

U.S. PATENT DOCUMENTS 6,522,333 B1 * 2/2003 Hatlelid .................. G06T 13/40
345/473
8,401,873 B2 3/2013 Brown et al.
(Continued)

FOREIGN PATENT DOCUMENTS

WO 03/104939 A2 12/2003
WO 2016007122 A1 1/2016

OTHER PUBLICATIONS

Kang, J., "Healthboard: A Graphic User Interface for Patient Centered Healthcare, the "Medical Home" Solution", Parsons Journal for Information Mapping, vol. VI, Issue 3, Summer 2014, pp. 1-14.
(Continued)

*Primary Examiner* — Michael Tomaszewski
*Assistant Examiner* — Jay M. Patel
(74) *Attorney, Agent, or Firm* — Honigman LLP; Grant Griffith

(57) ABSTRACT

The present system is configured to track informal observations by multiple caregivers about a care recipient and provide actionable feedback to the multiple caregivers for managing health of the care recipient based on the informal observations. Informal caregivers are constantly observing the health and/or wellness of care recipients they provide care for. Within families for example, multiple informal caregivers coordinate the care they provide for a care recipient amongst each other to balance the workload. These caregivers observe the same care recipient often on different occasions, from different perspectives, and with varying levels of subjectivity. Keeping an eye out for abnormal behavior by the care recipient, changes in capabilities of the care recipient, and/or potential disease progression, for
(Continued)

example, are pieces of data caregivers commonly observe in an informal, rarely structured way.

14 Claims, 13 Drawing Sheets

(51) Int. Cl.
  *G16H 50/70* (2018.01)
  *G06Q 10/06* (2012.01)
  *G16H 40/20* (2018.01)
  *G16H 40/63* (2018.01)
  *G16H 40/67* (2018.01)
(52) U.S. Cl.
  CPC ............. *G16H 40/63* (2018.01); *G16H 40/67* (2018.01); *G16H 50/70* (2018.01)

(56) References Cited

U.S. PATENT DOCUMENTS

| | | |
|---|---|---|
| 8,521,564 B1 | 8/2013 | Ciechannowski |
| 9,257,029 B1 | 2/2016 | Hendrick, III et al. |
| 2001/0039503 A1* | 11/2001 | Chan ...................... G16H 40/20 705/2 |
| 2005/0117527 A1* | 6/2005 | Williams ............. G06Q 10/107 370/260 |
| 2011/0161278 A1* | 6/2011 | Kawagishi .............. G06F 19/00 706/52 |
| 2012/0179485 A1 | 7/2012 | Saneii |
| 2012/0215557 A1 | 8/2012 | Flanagan et al. |
| 2012/0239434 A1 | 9/2012 | Breslow et al. |
| 2013/0065569 A1 | 3/2013 | Leipzig et al. |
| 2013/0071825 A1 | 3/2013 | Toda |
| 2013/0111353 A1* | 5/2013 | Ueda ................... G06F 3/04817 715/748 |
| 2013/0191140 A1 | 7/2013 | Fotheringham et al. |
| 2014/0142970 A1* | 5/2014 | Baronov .............. A61B 5/0205 705/2 |
| 2014/0324472 A1 | 10/2014 | Delaney et al. |
| 2015/0019912 A1* | 1/2015 | Darling ............... G06F 11/2257 714/26 |
| 2015/0187119 A1* | 7/2015 | Masumoto .............. G06T 11/00 345/424 |
| 2015/0286797 A1* | 10/2015 | Ratto ..................... G16H 40/67 705/2 |
| 2015/0379226 A1 | 12/2015 | Morinaga |
| 2016/0026706 A1* | 1/2016 | Lum ..................... G06F 16/955 707/740 |

OTHER PUBLICATIONS

Lin, et al., "Mobile Medical Management", Designs Specifications, Oct. 1, 2012, 16 pages.

* cited by examiner

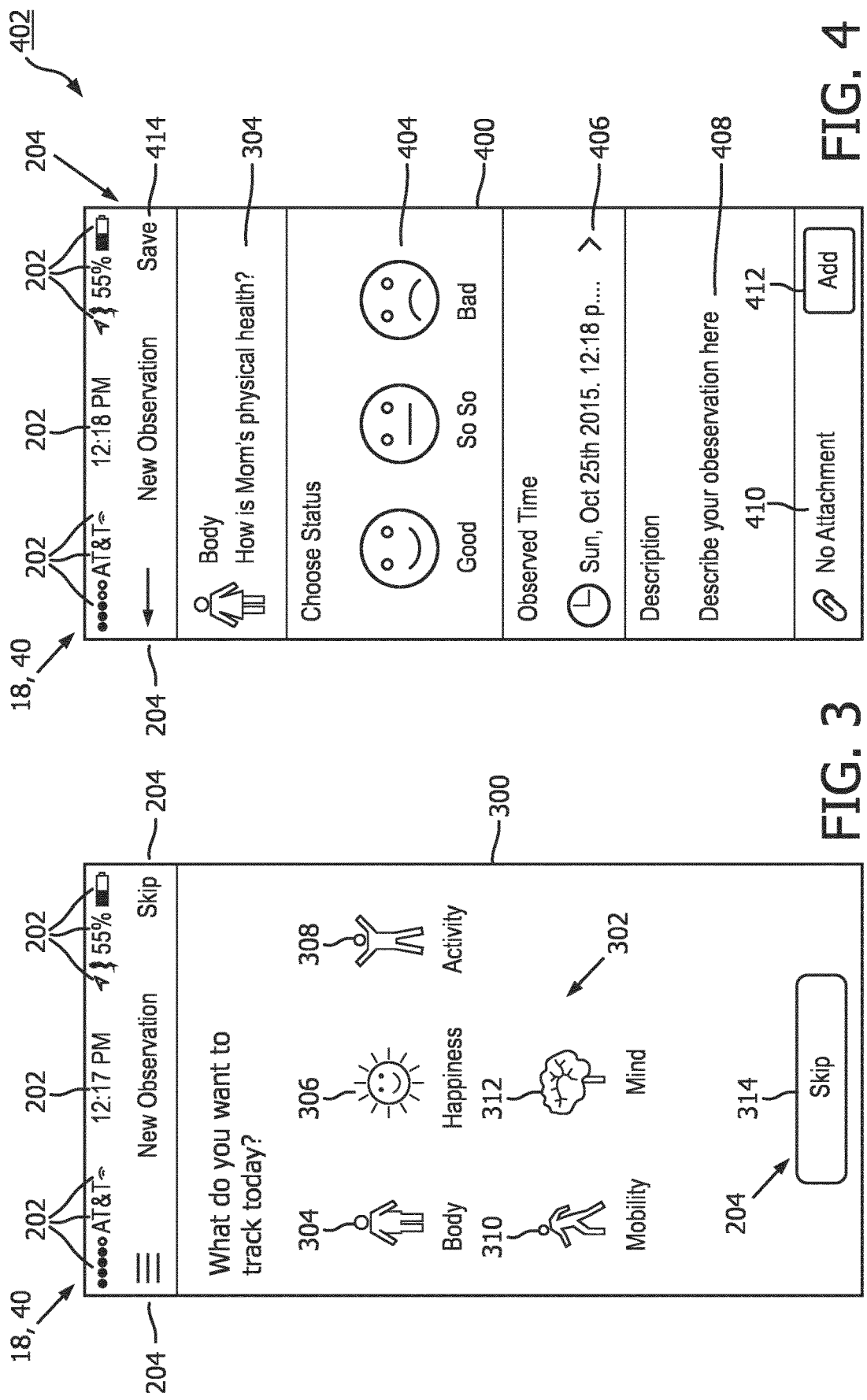

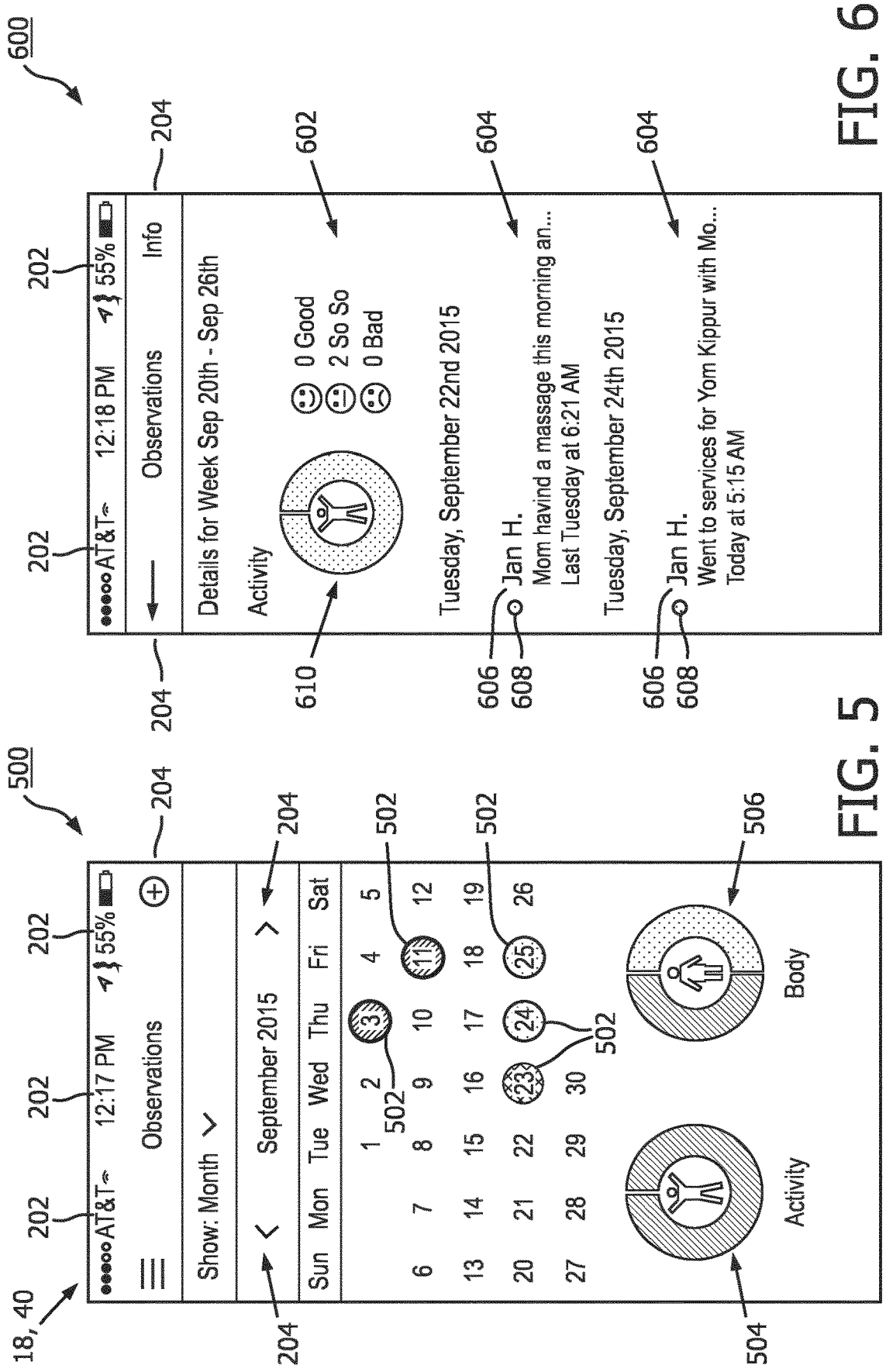

SYSTEM AND METHOD FOR TRACKING INFORMAL OBSERVATIONS ABOUT A CARE RECIPIENT BY CAREGIVERS

This application is the U.S. National Phase application under 35 U.S.C. § 371 of International Application No. PCT/EP2017/061242, filed on May 11, 2017, which claims the benefit of U.S. Provisional Application Ser. No. 62/335,972, filed May 13, 2016. These applications are hereby incorporated by reference herein.

BACKGROUND

1. Field

The present disclosure pertains to a system and method for tracking informal observations by multiple caregivers about a care recipient and providing actionable feedback to the multiple caregivers for managing health of the care recipient based on the informal observations.

2. Description of the Related Art

Typically, multiple informal caregivers are constantly observing the health and wellness of a care recipient. These observations can provide valuable information about the status of the care recipient. However, some seemingly small individual observation may go unshared resulting in a missed opportunity to prevent a serious event from occurring.

SUMMARY

Accordingly, one or more aspects of the present disclosure relate to a system configured to track informal observations by multiple caregivers about a care recipient and provide actionable feedback to the multiple caregivers for managing health of the care recipient based on the informal observations. The system comprises one or more hardware processors and/or other components. The one or more hardware processors are configured by machine readable instructions to obtain medical history information about the care recipient. The medical history information indicates the health of the care recipient including one or more medical conditions experienced by the care recipient. The one or more hardware processors are configured to cause presentation of a graphical user interface configured to facilitate entry and/or selection of the informal observations by the multiple caregivers. The graphical user interface is presented on individual computing devices associated with individual caregivers. The one or more hardware processors are configured to analyze the informal observations and the medical history information to determine one or more of a change in the health of the care recipient or a medical event experienced by the care recipient. The one or more hardware processors are configured to generate actionable feedback for the multiple caregivers based on the analysis. The actionable feedback comprises recommendations for managing the health of the care recipient and supporting content related to the recommendations. The supporting content comprises information related to the recommendations obtained from one or more external sources of data. The one or more hardware processors are configured to cause presentation of the actionable feedback to the multiple caregivers via the graphical user interface.

Another aspect of the present disclosure relates to a method for tracking informal observations by multiple caregivers about a care recipient and providing actionable feedback to the multiple caregivers for managing health of the care recipient based on the informal observations with an observation system. The system comprises one or more hardware processors and/or other components. The method comprises obtaining medical history information about the care recipient. The medical history information indicates the health of the care recipient including one or more medical conditions experienced by the care recipient. The method comprises causing presentation of a graphical user interface configured to facilitate entry and/or selection of the informal observations by the multiple caregivers. The graphical user interface is presented on individual computing devices associated with individual caregivers. The method comprises analyzing the informal observations and the medical history information to determine one or more of a change in the health of the care recipient or a medical event experienced by the care recipient. The method comprises generating actionable feedback for the multiple caregivers based on the analysis. The actionable feedback comprises recommendations for managing the health of the care recipient and supporting content related to the recommendations. The supporting content comprises information related to the recommendations obtained from one or more external sources of data. The method comprises causing presentation of the actionable feedback to the multiple caregivers via the graphical user interface.

Still another aspect of present disclosure relates to a system configured to track informal observations by multiple caregivers about a care recipient and provide actionable feedback to the multiple caregivers for managing health of the care recipient based on the informal observations. The system comprises means for obtaining medical history information about the care recipient. The medical history information indicates the health of the care recipient including one or more medical conditions experienced by the care recipient. The system comprises means for causing presentation of a graphical user interface configured to facilitate entry and/or selection of the informal observations by the multiple caregivers. The graphical user interface is presented on individual computing devices associated with individual caregivers. The system comprises means for analyzing the informal observations and the medical history information to determine one or more of a change in the health of the care recipient or a medical event experienced by the care recipient. The system comprises means for generating actionable feedback for the multiple caregivers based on the analysis. The actionable feedback comprises recommendations for managing the health of the care recipient and supporting content related to the recommendations. The supporting content comprises information related to the recommendations obtained from one or more external sources of data. The system comprises means for causing presentation of the actionable feedback to the multiple caregivers via the graphical user interface.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

BRIEF DESCRIPTION OF THE DRAWINGS

FIG. 3 illustrates an example view of a user interface that presents selectable observation categories to facilitate tracking observations about the care recipient.

FIG. 4 illustrates an example view of the user interface that presents observation entry and/or selection fields.

FIG. 5 illustrates a month overview of observations made by caregivers.

FIG. 6 illustrates a detailed week view of the activity observation category.

DETAILED DESCRIPTION OF EXEMPLARY EMBODIMENTS

Figure 1:
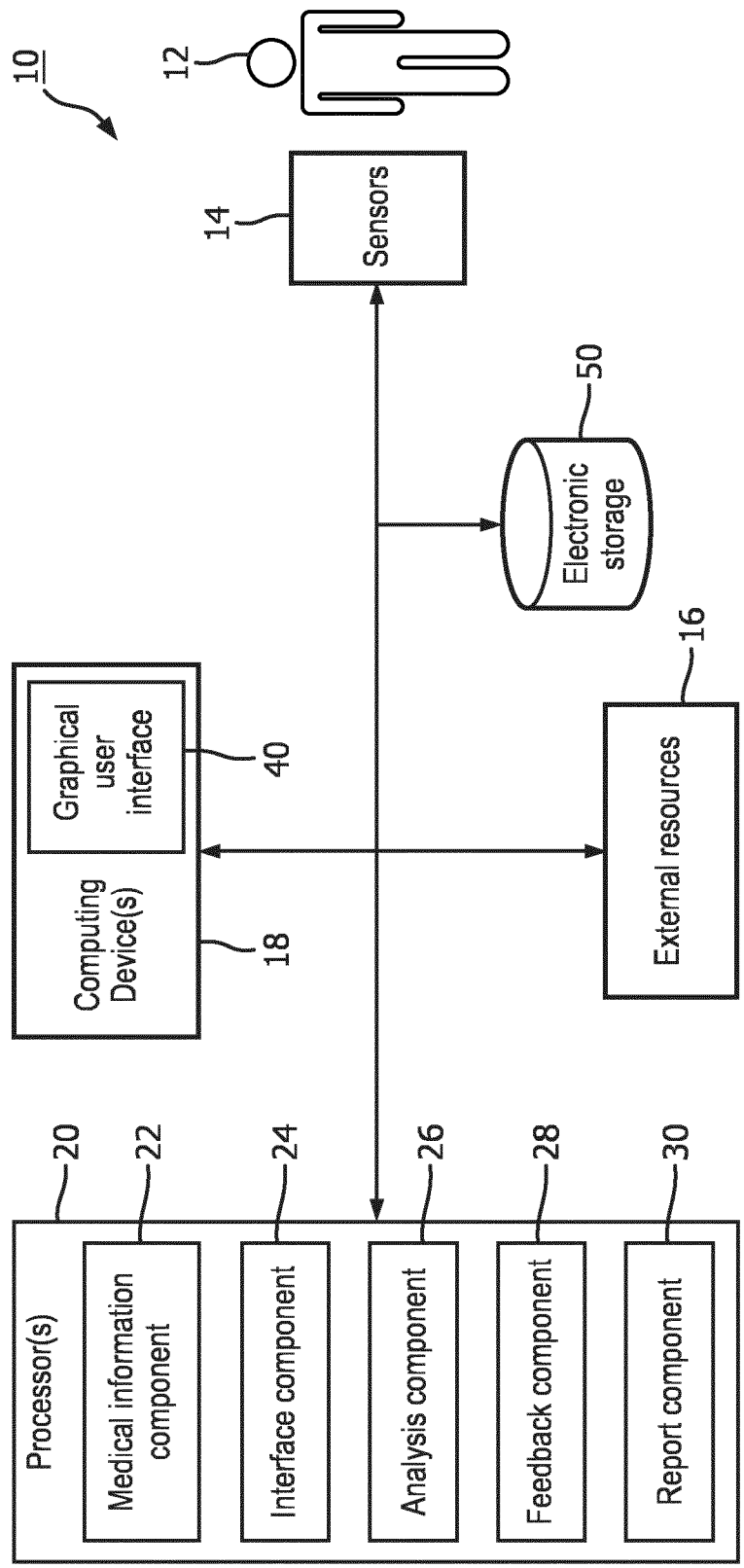
FIG. 1 is a schematic illustration of a system configured to track informal observations by multiple caregivers about a care recipient and provide actionable feedback to the multiple caregivers for managing health of the care recipient based on the informal observations.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to track informal observations by multiple caregivers about a care recipient 12 and provide actionable feedback to the multiple caregivers for managing health of care recipient 12 based on the informal observations. Informal caregivers regularly observe the health and/or wellness of care recipients they provide care for (e.g., care recipient 12). Within families for example, multiple informal caregivers coordinate the care they provide for a care recipient (e.g., care recipient 12) amongst each other to balance the workload. These caregivers observe the same care recipient often on different occasions (e.g., daily, weekly, sporadically during the month, etc.), from different perspectives (e.g., telephone calls, face-to-face visits, as a close friend, as a daughter, a son, etc.) and with varying levels of subjectivity (e.g., individual caregivers may have a different perception of what "bad" and/or "worse" means, different levels of perceived concern, etc.). Keeping an eye out for abnormal behavior by care recipient 12, changes in capabilities of care recipient 12, and/or potential disease progression, for example, are pieces of data caregivers commonly observe in an informal, unstructured way.

Any single observation, for example witnessing care recipient 12 trip, may not warrant contact by a caregiver to an entire care circle (e.g., the group of caregivers caring for care recipient 12) to report the event. However, if the same behavior (e.g., tripping) is observed by other caregivers on separate occasions, there may be cause for concern. Unfortunately, there is no existing mechanism to give multiple caregivers the ability to log their individual observations of care recipient 12 tripping (in this example) without raising potential undue concern. However, if the tripping observations are not logged, the pattern goes unnoticed and it isn't until care recipient 12 has a fall resulting in an injury that caregivers piece things together. Had the observations been shared, the caregivers may have been able to prevent the fall from occurring.

System 10 facilitates logging of observations from multiple caregivers, finding patterns within data conveyed by the observations, and notifying caregivers of potential declining health of care recipient 12, and/or medical events experienced by care recipient 12. System 10 provides a solution for data loss and/or communication loss that occurs within families caring for a sick and/or elder, for example, loved one (e.g., care recipient 12). Data is aggregated and displayed by system 10 in a way that allows informal caregivers to see the wellness of their loved one over time. System 10 facilitates logging of observations of care recipient 12 by multiple caregivers, viewing and/or reflecting on observations made by fellow caregivers, viewing trends in care recipient 12 well-being, generating a report that can be shared with the care recipient's healthcare professionals, and/or other activities.

The caregivers may include medical and/or social care staff; home health staff; nurses; doctors; parents, children, grandchildren, and/or other caregiving relatives; neighbors; friends; and/or other caregivers. In general, the caregivers may include any person capable of making observations about care recipient 12. In some embodiments, system 10 includes one or more of sensors 14, external resources 16, computing devices 18, processors 20, electronic storage 50, and/or other components.

Sensors 14 are configured to generate output signals that convey information related to the heath of care recipient 12. In some embodiments, sensors 14 include but are not limited to equipment used in hospitals, doctor's offices, and/or other medical facilities to monitor vital signs and/or other physiological information (e.g., pulse rate monitors, blood pressure monitors, blood oxygenation monitors, glucose monitors, weight scales, thermometers, electrocardiogram (EKG) equipment, childbirth labor contraction monitors, etc.), test equipment (e.g., imaging equipment such as an MRI and/or an x-ray machine, an ultrasound, electroencephalogram (EEG) equipment, etc.), equipment for treating subject 12 (e.g., respirators/ventilators, light therapy devices, etc.), devices for entering and/or selecting information (e.g., desktop computers, laptop computers, tablet computers, smartphones, cameras, video equipment, etc.) associated with subject 12, and/or other devices.

External resources 16 include sources of information (e.g., databases, websites, etc.), external entities participating with system 10 (e.g., a medical records system of a health care provider that stores medical history information for care recipient 12), external home monitoring systems, one or more servers outside of system 10, a network (e.g., the internet), electronic storage, equipment related to Wi-Fi technology, equipment related to Bluetooth® technology, data entry devices, sensors, scanners, and/or other resources. For example, in some embodiments, external resources 16 may include a database where medical history information for care recipient 12 and/or other care recipients are stored, and/or other sources of information. In some implementations, some or all of the functionality attributed herein to external resources 16 may be provided by resources included in system 10. External resources 16 may be configured to communicate with processor 20, computing devices 18, sensors 14, electronic storage 50, and/or other components of system 10 via wired and/or wireless connections, via a network (e.g., a local area network and/or the internet), via cellular technology, via Wi-Fi technology, and/or via other resources.

Computing devices 18 are configured to provide interfaces between multiple caregivers, care recipient 12, and/or other users and system 10. In some embodiments, individual computing devices 18 are associated with individual caregivers 18, care recipient 12, and/or other users. Computing devices 18 are configured to provide information to and/or receive information from the caregivers, care recipient 12, and/or other users. For example, computing devices 18 are configured to present a graphical user interface 40 to the caregivers to facilitate entry and/or selection of observations about care recipient 12. In some embodiments, graphical user interface 40 includes a plurality of separate interfaces associated with computing devices 18, processor 20 and/or other components of system 10, for example.

In some embodiments, computing devices 18 are configured to provide graphical user interface 40, processing capabilities, databases, and/or electronic storage to system 10. As such, computing devices 18 may include processors 20, electronic storage 50, external resources 16, sensors 14, and/or other components of system 10. In some embodiments, computing devices 18 are connected to a network (e.g., the internet). In some embodiments, computing devices 18 do not include processors 20, electronic storage 50, external resources 16, sensors 14, and/or other components of system 10, but instead communicate with these components via the network. The connection to the network may be wireless or wired. For example, processor 20 may be located in a remote server and may wirelessly cause display of graphical user interface 40 to the caregivers on computing devices 18. In some embodiments, an individual computing device 18 is a laptop, a personal computer, a smartphone, a tablet computer, and/or other computing devices. Examples of interface devices suitable for inclusion in an individual computing device 18 include a touch screen, a keypad, touch sensitive and/or physical buttons, switches, a keyboard, knobs, levers, a display, speakers, a microphone, an indicator light, an audible alarm, a printer, and/or other interface devices. The present disclosure also contemplates that an individual computing device 18 includes a removable storage interface. In this example, information may be loaded into a computing device 18 from removable storage (e.g., a smart card, a flash drive, a removable disk) that enables the caregivers, care recipient 12, and/or other users to customize the implementation of computing devices 18. Other exemplary input devices and techniques adapted for use with computing devices 18 include, but are not limited to, an RS-232 port, RF link, an IR link, a modem (telephone, cable, etc.) and/or other devices.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., a server), or processor 20 may represent processing functionality of a plurality of devices operating in coordination (e.g., one or more servers, one or more computing devices 18 associated with caregivers, a computing device associated with care recipient 12, and/or other users, sensors 14, devices that are part of external resources 16, electronic storage 50, and/or other devices.)

In some embodiments, processor 20, sensors 14, external resources 16, computing devices 18, electronic storage 50, and/or other components may be operatively linked via one or more electronic communication links. For example, such electronic communication links may be established, at least in part, via a network such as the Internet, and/or other networks. It will be appreciated that this is not intended to be limiting, and that the scope of this disclosure includes embodiments in which these components may be operatively linked via some other communication media. In some embodiments, processor 20 is configured to communicate with sensors 14, external resources 16, computing devices 18, electronic storage 50, and/or other components according to a client/server architecture, a peer-to-peer architecture, and/or other architectures.

As shown in FIG. 1, processor 20 is configured via machine-readable instructions to execute one or more computer program components. The one or more computer program components may comprise one or more of a medical information component 22, an interface component 24, an analysis component 26, a feedback component 28, a report component 30, and/or other components. Processor 20 may be configured to execute components 22, 24, 26, 28, and/or 30 by software; hardware; firmware; some combination of software, hardware, and/or firmware; and/or other mechanisms for configuring processing capabilities on processor 20.

It should be appreciated that although components 22, 24, 26, 28, and 30 are illustrated in FIG. 1 as being co-located within a single processing unit, in embodiments in which processor 20 comprises multiple processing units, one or more of components 22, 24, 26, 28, and/or 30 may be located remotely from the other components. The description of the functionality provided by the different components 22, 24, 26, 28, and/or 30 described below is for illustrative purposes, and is not intended to be limiting, as any of components 22, 24, 26, 28, and/or 30 may provide more or less functionality than is described. For example, one or more of components 22, 24, 26, 28, and/or 30 may be eliminated, and some or all of its functionality may be provided by other components 22, 24, 26, 28, and/or 30. As another example, processor 20 may be configured to execute one or more additional components that may perform some or all of the functionality attributed below to one of components 22, 24, 26, 28, and/or 30.

Medical information component 22 is configured to obtain medical history information about care recipient 12. The medical history information indicates the health of care recipient 12 including one or more medical conditions experienced by care recipient 12, and/or other medical history information. Indicating the health of care recipient 12 may include conveying information related to vital signs of care recipient 12, a physical condition of subject 12, medical records describing previous medical treatment provided to subject 12, and/or other information. The one or more medical conditions experienced by care recipient 12 include diseases care recipient 12 has been diagnosed with (e.g., heart disease, cancer, anemia, chronic obstructive pulmonary disease, HIV/AIDS, dementia, Alzheimer's, diabetes, etc.), injuries suffered by care recipient 12 (e.g., broken bones, concussions, nerve damage, trauma, joint injuries, sprained ligaments, etc.); ailments (e.g., arthritis, asthma, strokes, osteoporosis, depression, skin conditions, heart burn, etc.), sicknesses (e.g., influenza, pneumonia, the common cold, etc.), and/or other information. In some embodiments, the medical history information is obtained from one or more external databases included in external resources 16 (e.g., a medical records database associated with a health care provider), electronic storage 50 included in system 10, one or more sensors 14, and/or other sources of the medical history information.

In some implementations, medical information component 22 is configured such that obtaining medical history information includes facilitating a caregiver portal software application. The caregiver portal software application may be accessed by the caregivers, care recipient 12, and/or other users via graphical user interface 40 and/or computing devices 18. The caregiver portal software application provides an electronic platform for caregivers to coordinate care provided to care recipient 12. In the application, caregivers are organized in care circles based on the person they are providing care for (e.g., care recipient 12). Caregivers are able to voluntarily contribute to the care recipient's care by accepting care tasks assigned through the application. Examples of things a caregiver can volunteer for include picking up groceries for care recipient 12, completing housework for care recipient 12, providing transportation to a doctor appointment for care recipient 12, and/or other tasks. The caregiver portal software application comprises a care recipient profile which includes information about the medical conditions experienced by care recipient 12, the previous observations logged by the caregivers, tasks performed by the caregivers for care recipient 12, upcoming tasks to be performed for care recipient 12, upcoming appointments on a calendar associated with care recipient 12, and/or other information. Medical information component 22 is configured such that information related to the medical conditions experienced by care recipient 12, one or more care circles associated with care recipient 12, upcoming tasks and/or tasks performed by caregivers for care recipient 12, upcoming appointments for care recipient 12, and/or other information is included in the obtained medical history information.

Interface component 24 is configured to cause presentation of graphical user interface 40 to facilitate entry and/or selection of observations (e.g., which are received by system 10) by the caregivers. As described herein, graphical user interface 40 is presented on one or more computing devices 18 associated with individual caregivers. Graphical user interface 40 is configured to receive the informal observations about care recipient 12. In some embodiments, the observations include one or more of textual descriptive notes, ratings, dates of the observations, times of the observations, visual images related to the observations, and/or other observations. Graphical user interface 40 is configured to facilitate entry and/or selection of the informal observations by the multiple caregivers. Graphical user interface 40 comprises one or more views corresponding to one or more observation categories, and one or more fields within an individual view corresponding to textual descriptive notes, ratings, dates, times, visual images, and/or other observations. In some embodiments, responsive to the entry and/or selection of the observations, one or more follow up questions based on the observations are presented via graphical user interface 40.

In some embodiments, interface component 24 is configured such that the one or more views include one or more landing page views configured to facilitate entry and/or selection of new observations by caregivers. In some embodiments, interface component 24 is configured such that the views of user interface 40 and/or the observations are organized into categories. These categories may be related to the body, mind, activity, mobility, happiness, comfort, and/or other characteristics of care recipient 12. For example, the categories may include but are not limited to "body," "happiness," "activity," "mobility," "mind," "comfort," and/or other categories. In some embodiments, interface component 24 is configured such that, in a given view of user interface 40, a caregiver selects a category (e.g., via a category selection field of the given view) for which he or she would like to make observations. Interface component 24 is configured such that additional observation categories may be added and/or current observation categories may be removed to customize the observations being collected. The categories may be added and/or removed as necessary by the caregivers, care recipient 12, and/or other users via entries and/or selections made using computing devices 18 and/or graphical user interface 40. Adding and/or removing categories may accommodate scenarios where a category of observations need only be tracked temporarily. For example, a doctor may request that caregivers make observations related to side effects of medication until the next visit to the doctor by care recipient 12. In response, a caregiver may add a temporary "side effects" observation category for the requested observations. In some embodiments, interface component 24 is configured to facilitate entry and/or selection of observations by the caregivers unrelated to any category.

Interface component 24 is configured such that category selection by a caregiver causes graphical user interface 40 to display a subsequent view to the caregiver where entry and/or selection of information related to the observation is captured via one or more entry and/or selection fields. In some embodiments, the entry and/or selection fields related to the observation include one or more of a rating field, a date and/or time field, description field, an image acquisition field, and/or other fields for an individual observation. In some embodiments, interface component 24 is configured such that ratings entered via a ratings field are in the form of emojis, text, numerical entries, and/or other formats. By way of a non-limiting example, rating emojis may include a green smiley face representing a rating of "good/better", a yellow neutral face representing a rating of "so-so/same", and/or a red frowning face to represent a rating of "bad/worse". Entries and/or selections made via a description field may provide context for other caregivers to interpret the rating. This may be helpful because two different caregivers making observations about the same characteristics of care recipient 12 observed at the same time may perceive (e.g., rate) the characteristics differently.

In some embodiments, interface component 24 is configured to present additional questions to a caregiver via one or more fields of a view of graphical user interface 40. The questions may be configured to facilitate gathering additional actionable information from the caregiver. This may enhance the structure of the information collected (e.g., enhance categorization of the observation, link the observation with other observations from the same caregiver and/or other caregivers, rank observations relative to each other, etc.), enhance quality of the analysis performed by analysis component 26 (described below), and/or have other effects.

In some embodiments, interface component 24 is configured to cause graphical user interface 40 to present one or more summary views of the observations to caregivers, care recipient 12, and/or other users. For example, interface component 24 is configured such that entry and/or selection of commands and/or requests via one or more fields of one of more views of graphical user interface 40 may cause graphical user interface 40 to present a day by day, week by week, month by month, year by year, category by category, caregiver by caregiver, etc., overview of observations received from the caregivers. In a view of a given summary, a caregiver may enter and/or select (e.g., via a corresponding selection field) a specific observation and/or observation category, and be provided with detailed information on the observations for that category (e.g., via a subsequent view and/or field that appear as a result of the selection).

In some embodiments, interface component 24 is configured such that one or more caregivers and/or care recipient 12 is designated as an administrator. The designated administrator may be determined at manufacture of system 10, determined via entries and/or selections made by care recipient 12 and/or caregivers via computing devices 18, and/or determined in other ways. Interface component 24 is configured such that the administrator has the ability to control (e.g., via entries and/or selections made via graphical user interface 40) the level of access (e.g., read only access, read/write access, etc.) to one or more views and/or fields of graphical user interface 40 that other caregivers have. For example, the observation category "body" may include observations related to pain felt by care recipient 12. Observations in this category may be accessible to all of the caregivers in the care circle for care recipient 12 so the caregivers can view observations made by any caregiver and track their own observations. As another example, observations in a "mind" observation category may reflect concerns caregivers have about dementia and/or other cognitive conditions. Interface component 24 is configured such that the administrator can decide to hide (e.g., via entries and/or selections made via graphical user interface 40) this category from care circle member caregivers for whom such information is not necessary (e.g., grandchildren, a neighbor, etc.). This facilitates continued reception of observations from such blocked caregivers while still protecting the privacy of care recipient 12.

FIG. 2-FIG. 13 illustrate various views and fields of graphical user interface 40. The views illustrated in FIG. 2-FIG. 13 are examples and are not intended to be limiting. The views and fields of graphical user interface 40 in FIG. 2-FIG. 13 are presented to caregivers, care recipient 12, and/or other users on a computing device 18 comprising a smartphone associated with an individual caregiver (but this is not intended to be limiting). Caregivers, care recipient 12, and/or other user may navigate between the views shown in FIG. 2-FIG. 13 and/or other views using navigation fields shown in FIG. 2-FIG. 13 and or other fields, and/or via other commands and/or prompts entered and/or selected via graphical user interface 40, computing devices 18, and/or other computing devices (e.g., this disclosure should not be limited to only the navigation fields shown in FIG. 3-FIG. 13).

Figure 2:
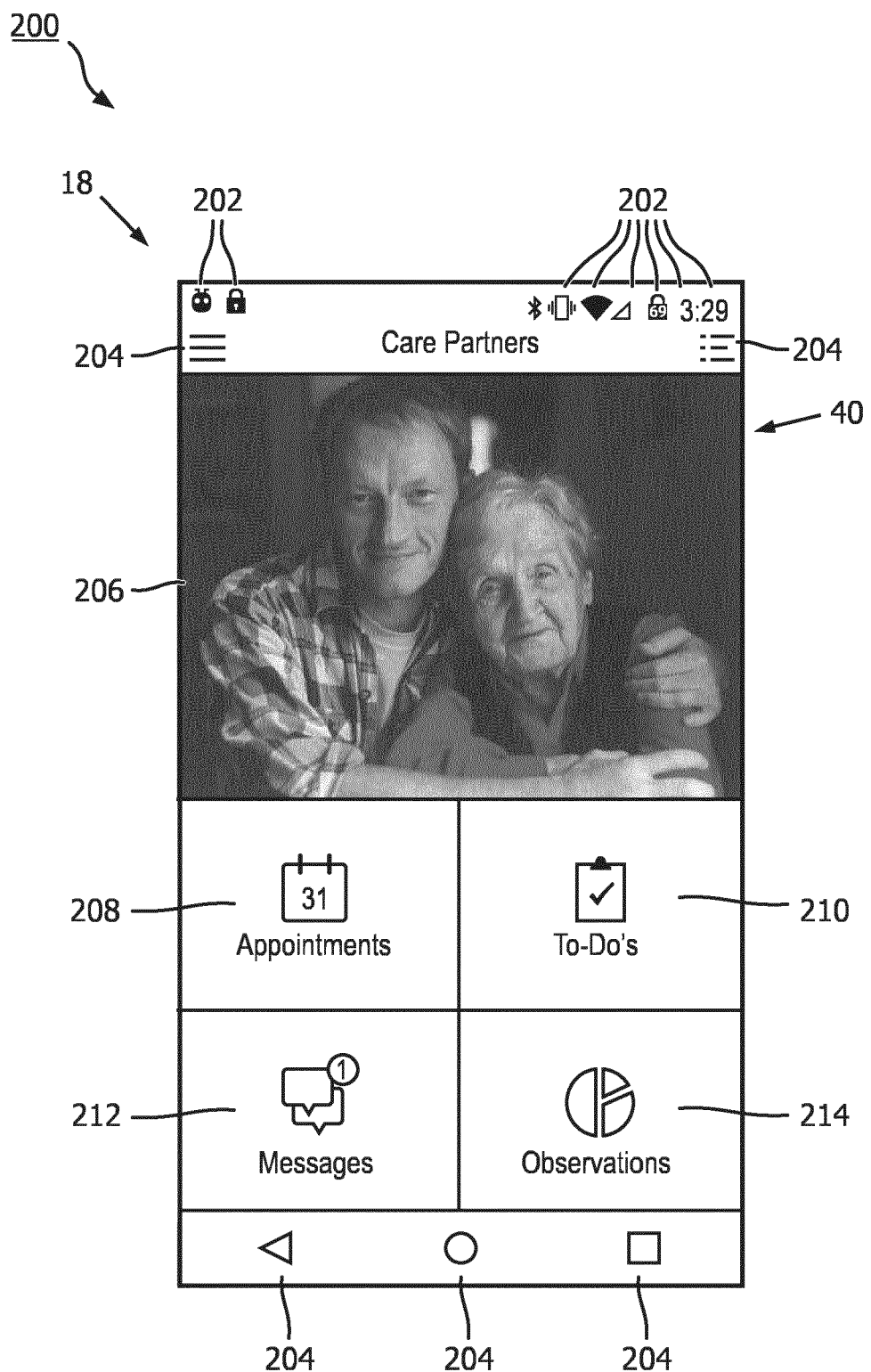
FIG. 2 illustrates a landing page view of a caregiver portal software application.

FIG. 2 illustrates a landing page view 200 of the caregiver portal software application. View 200 includes smartphone status fields 202, navigation fields 204, an image display field 206, an appointment field 208, a to-do field 210, a messages field 212, and an observations field 214. Smartphone status fields 202 indicate a status of various functions performed by the smartphone (e.g., a Wi-Fi and/or Bluetooth connectivity, a power level, etc.). Navigation fields 204 facilitate view to view navigation within the caregiver portal software application. Image display field 206 displays a background and/or title image for the caregiver portal software application. Appointment field 208, to-do field 210, and/or messages field 212 facilitate coordination of care provided to care recipient 12 (shown in FIG. 1) by the caregivers (e.g., in a care circle associated with care recipient 12). A list of appointments for care recipient 12 may be accessed via appointment field 208. A list of tasks to be performed to care for care recipient 12 may be accessed via to-do field 210. Messages between caregivers and/or care recipient 12 may be accessed via messages field 12. As shown in FIG. 2, the caregiver associated with this particular computing device 18 has a pending message indicated by the "1" in field 212. A caregiver may log observations about care recipient 12 as described herein via observations field 214.

FIGS. 3 and 4 illustrate example views 300 and 400 of user interface 40 that facilitate tracking observations about care recipient 12 (FIG. 1). View 300 presents selectable observation category fields 302 for a new observation. The selectable observation category fields 302 include a "body" category field 304, a "happiness" category field 306, an "activity" category field 308, a "mobility" category field 310, and a "mind" category field 312. In some embodiments, caregivers may utilize "skip" field 314 to log (e.g., enter and/or select information related to) observations without categorizing the observations.

View 400 presents observation entry and/or selection fields 402 for the "body" observation category 304. View 400 may be accessed, for example by selecting "body" category field 304 in view 300. Caregivers may provide a rating via rating field 404, a date and/or time via date/time field 406, description via description field 408, an image and/or other attachments via attachment field 410, and/or other information for the new observation. As shown in FIG. 4, in some embodiments, ratings are selected via emojis with a green smiley face representing a rating of "good", a yellow neutral face representing a rating of "so-so" and a red frowning face to represent a rating of "bad". Caregivers may "add" the new observation to other observations about care recipient 12 (FIG. 1) received by system 10 via "add" field 412. Caregivers may save an in progress observation via "save" field 414.

FIG. 5 and FIG. 6 illustrate portions of views 500 and 600 presented to caregivers to summarize observations made by the caregivers. View 500 illustrates a month (e.g., September) overview of observations made by caregivers. In this example, a colored circle 502 on a date indicates that there was at least one observation made on that day, and the color of the circle indicates the lowest rated observation for that day over all of the observation categories. View 500 provides quick visual information to a given caregiver that communicates the number of days that observations were made and roughly the overall rating for the care recipient in that month. Fields 504 and 506 summarize ratings by observation category for the month. For example, ratings in activity observations (field 504) for September were 100% good (e.g., as indicated by the entirety of the green circle around the activity icon). Ratings in body observations (field 506) for September were approximately 50% good and 50% so-so.

View 600 illustrates a detailed week view of the activity observation category. An activity observation count by rating field 602 is shown along with description fields 604, author (e.g., caregiver) fields 606, and rating fields 608 for two individual observations in that week. Field 610 summarizes activity observation ratings for this particular week.

Figure 7:
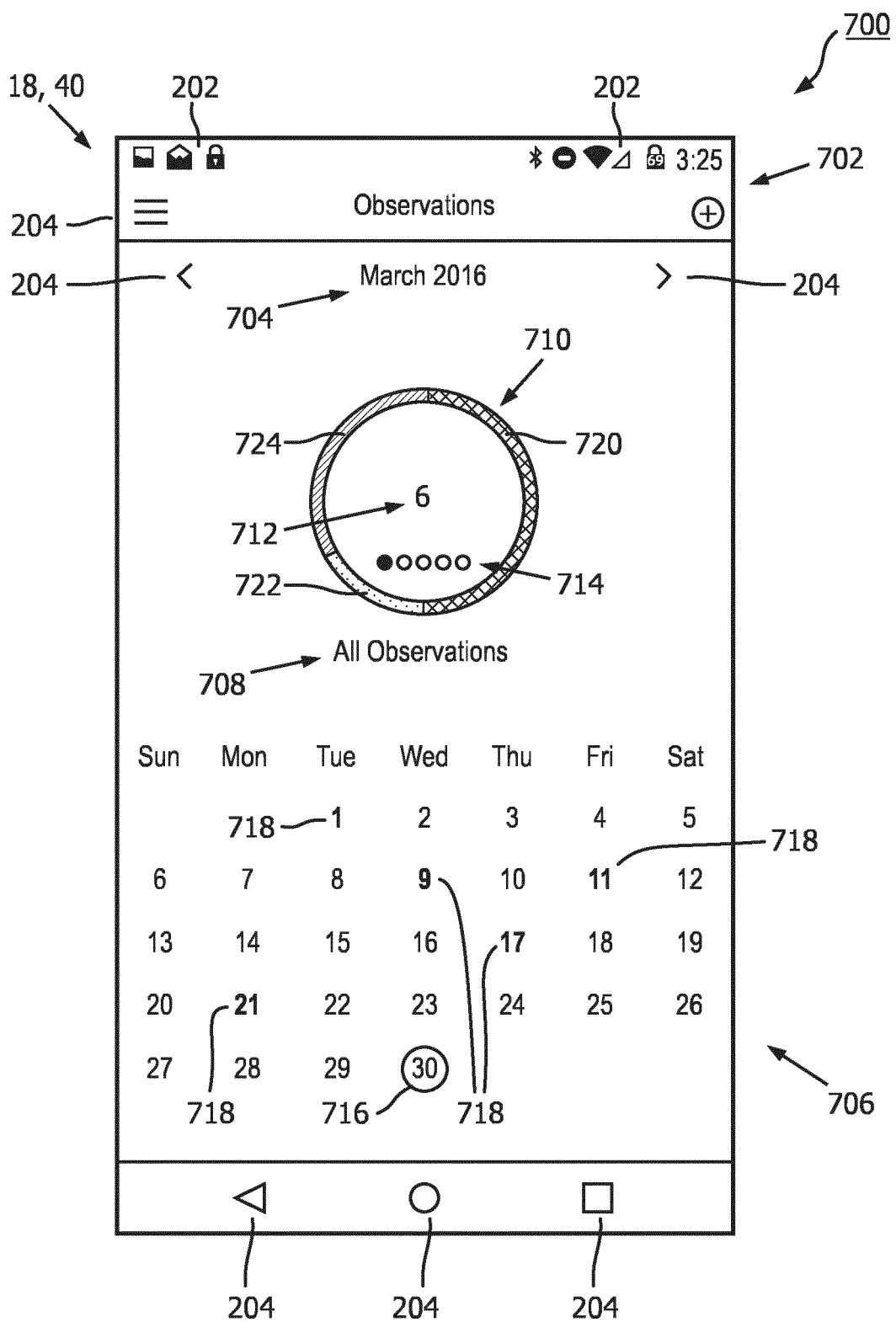
FIG. 7 illustrates a summary view of observations for one month.
Figure 8:
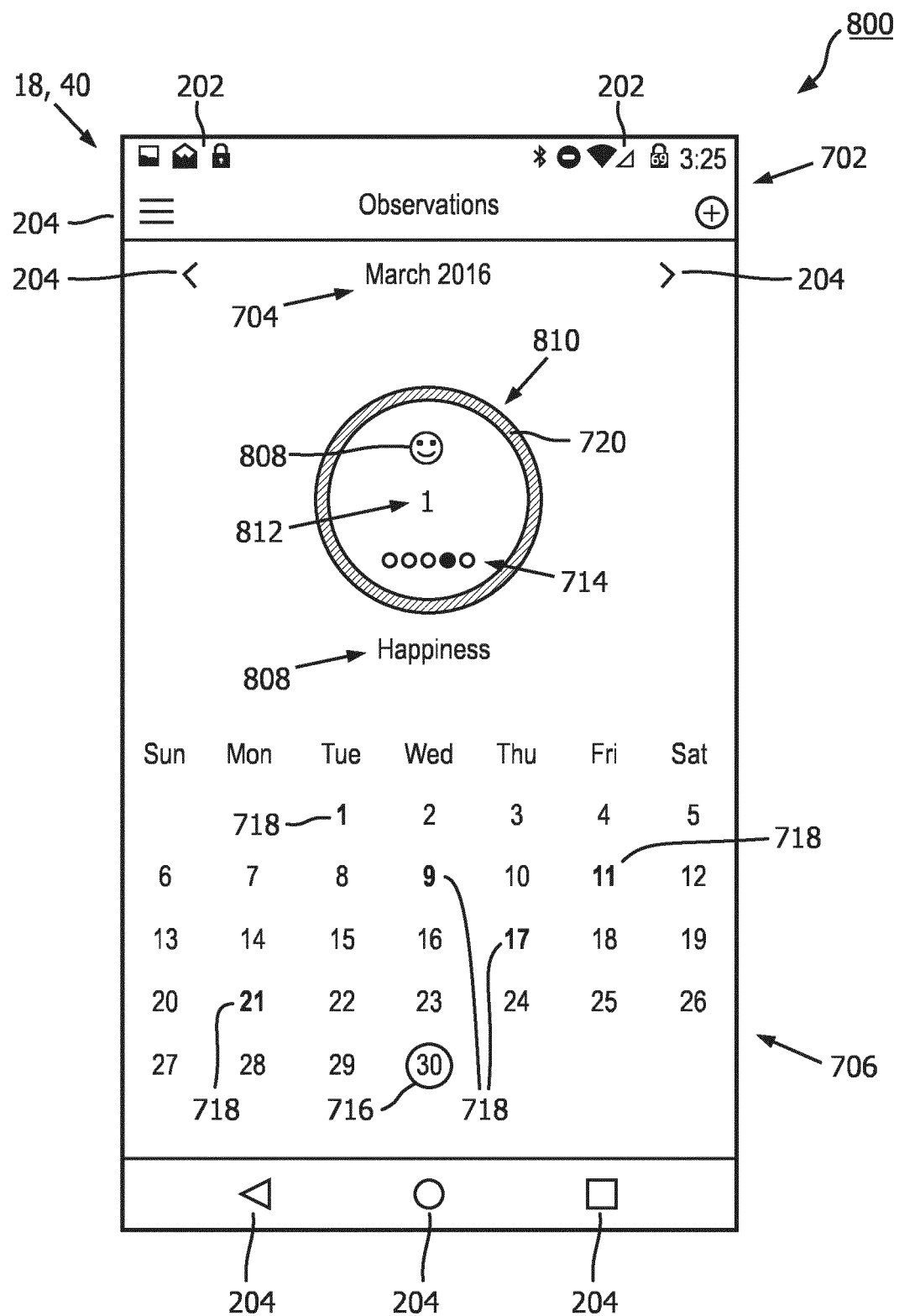
FIG. 8 illustrates a summary view of happiness observations for the month.
Figure 9:
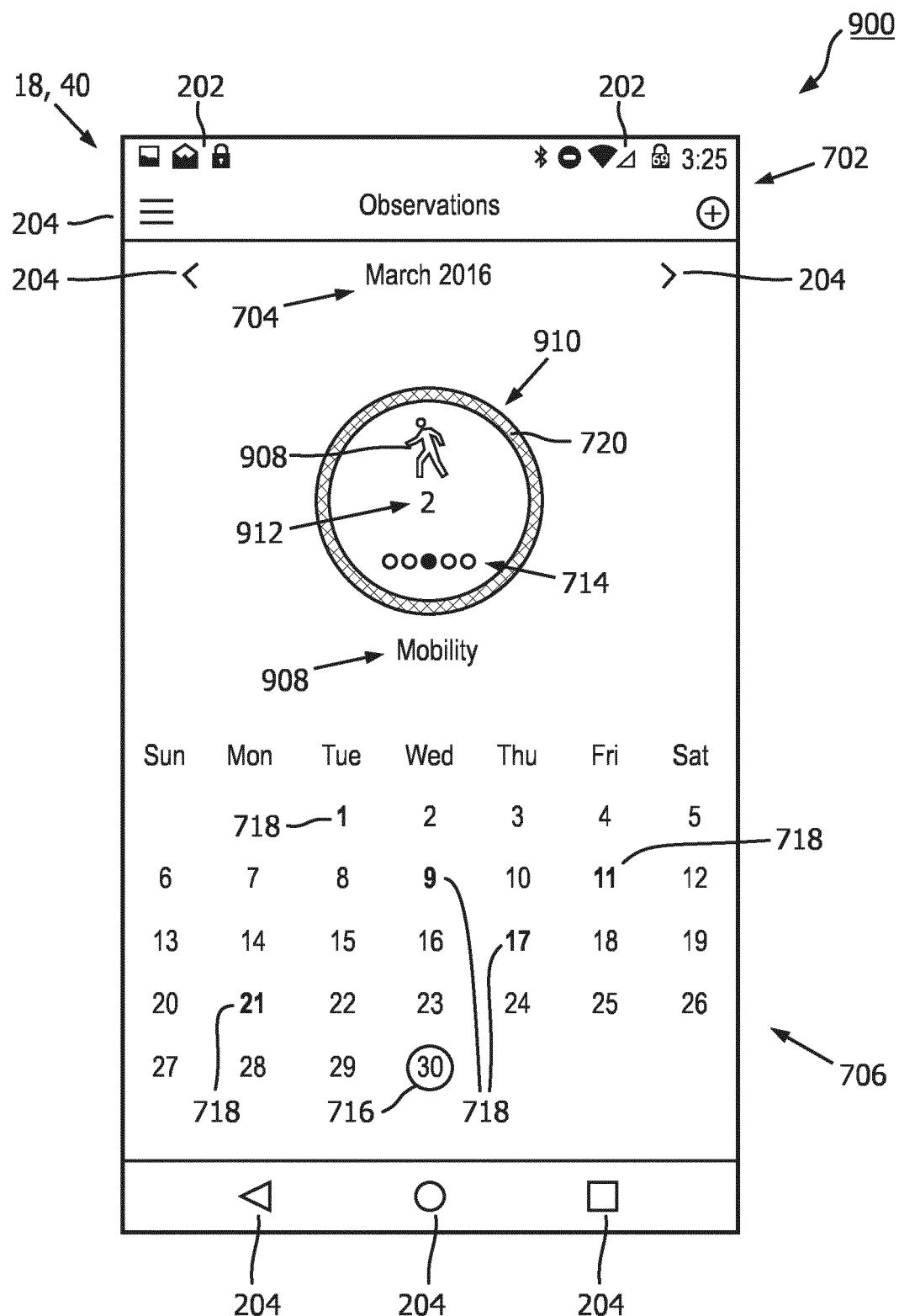
FIG. 9 illustrates a summary view of mobility observations for the month.
Figure 10:
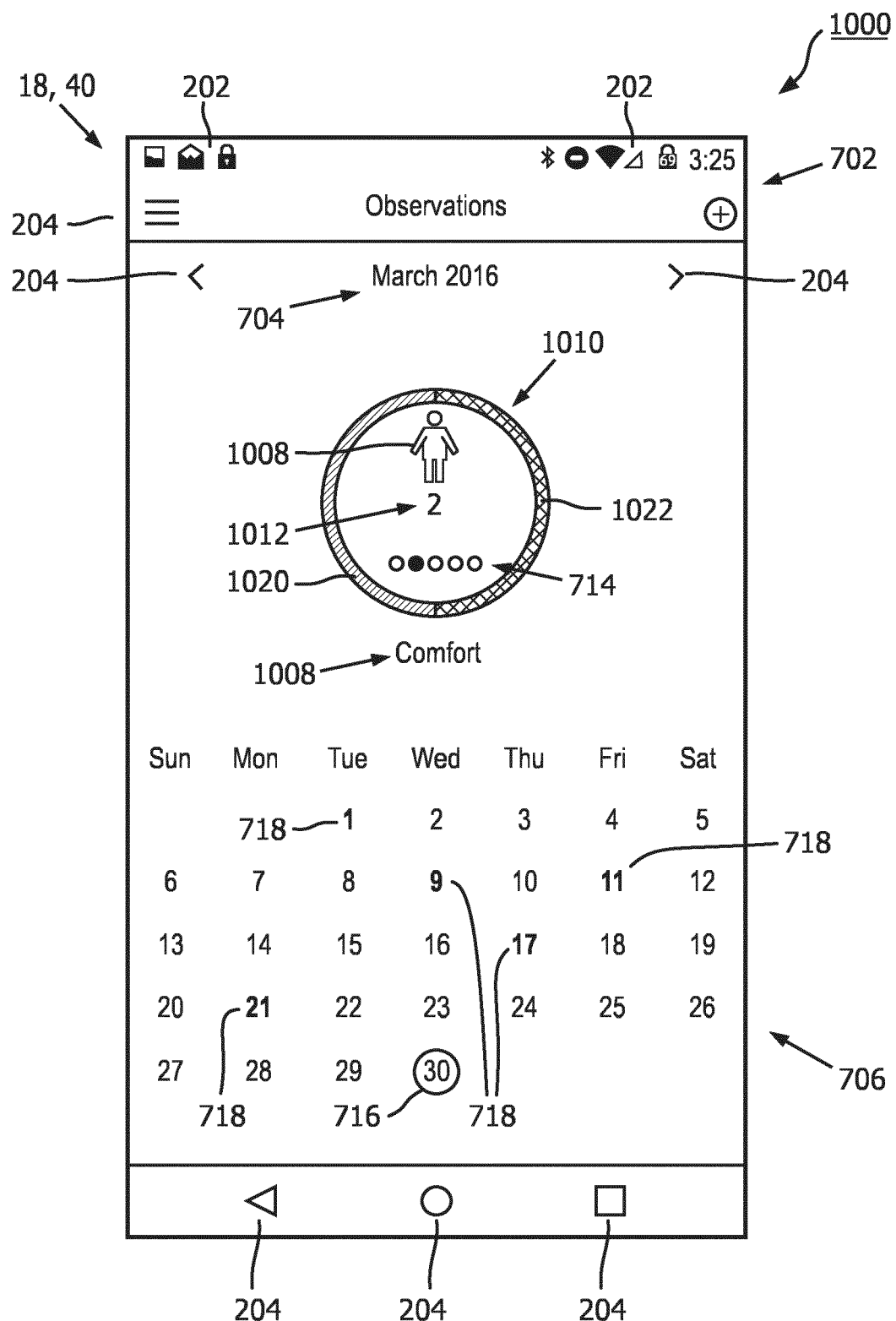
FIG. 10 illustrates a summary view of comfort observations for the month.

FIG. 7-FIG. 10 illustrate summary views 700, 800, 900, and 1000 of observations for the month of March 2016. Summary views 700-1000 include a new observation generation field 702; a date field 704; a calendar field 706; observation category fields 708, 808, 908, and 1008; color coded ratings summary fields 710, 810, 910, and 1010; number of ratings per category fields 712, 812, 912, and 1012; and a view to view navigation indicator field 714. Calendar field 706 includes a current date indicator 716 and indicators 718 showing which individual days of the month when observations were received by system 10 (FIG. 1). As shown in FIG. 7, six total observations were received in March 2016. About half of them were rated "bad/worse" (red portion 720 of rating summary field 710), about one sixth of them were rated "so-so/same" (yellow portion 722 of rating summary field 710), and about one third of them were rated "good/better" (green portion 724 of rating summary field 710). As shown in FIG. 8, one total happiness observation was received. The one happiness observation was rated "good/better". As shown in FIG. 9, two total mobility observations were received. Both mobility observations were rated "bad/worse". As shown in FIG. 10, two total comfort observations were received. One comfort observation was rated "good/better" (e.g., half 1020 of the circle is green), and one comfort observation was rated "bad/worse" (e.g., the other half 1022 of the circle is red).

Figure 11:
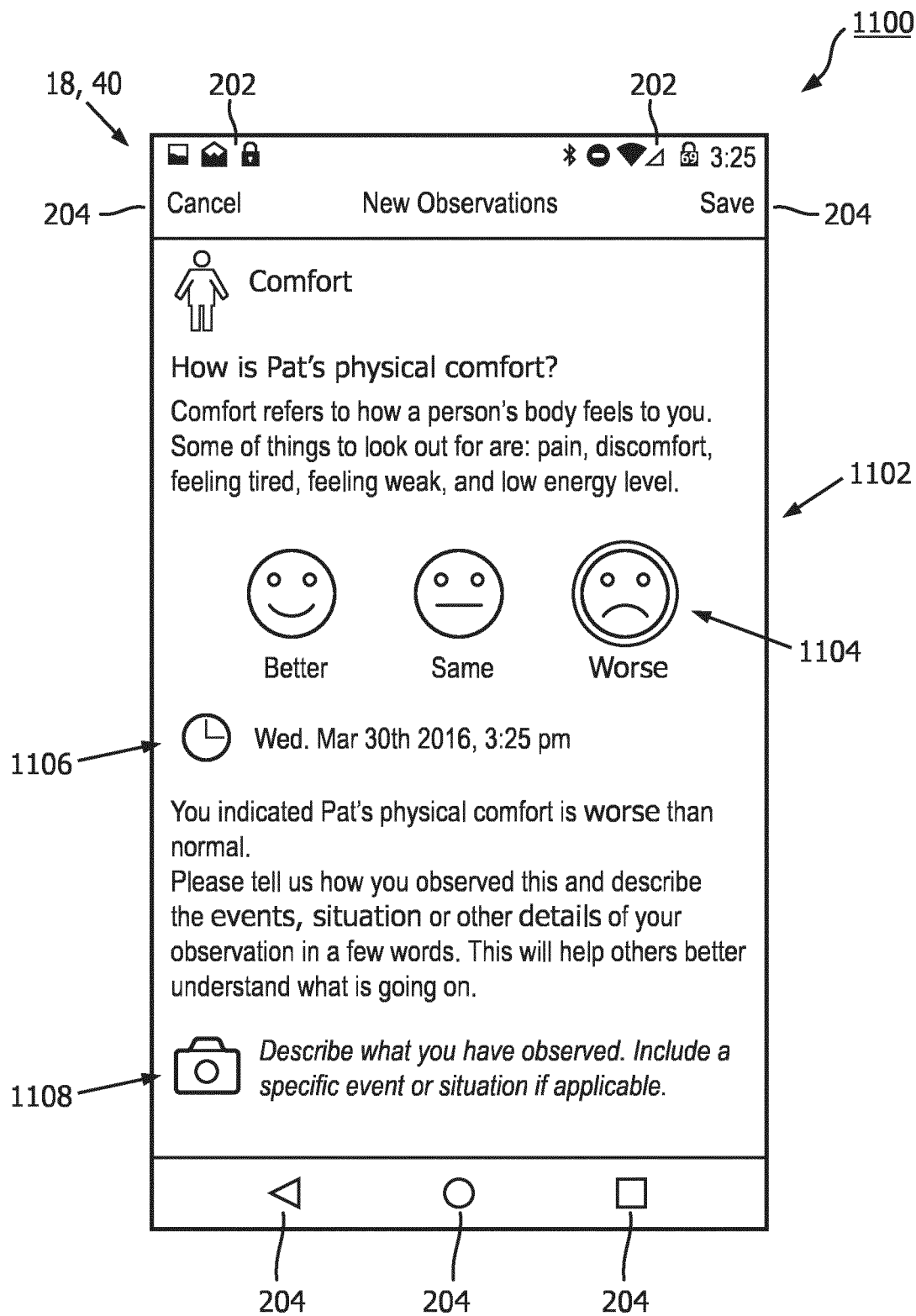
FIG. 11 illustrates a second example of many possible views configured to receive entry and/or selection of information related to the observations by caregivers.
Figure 12:
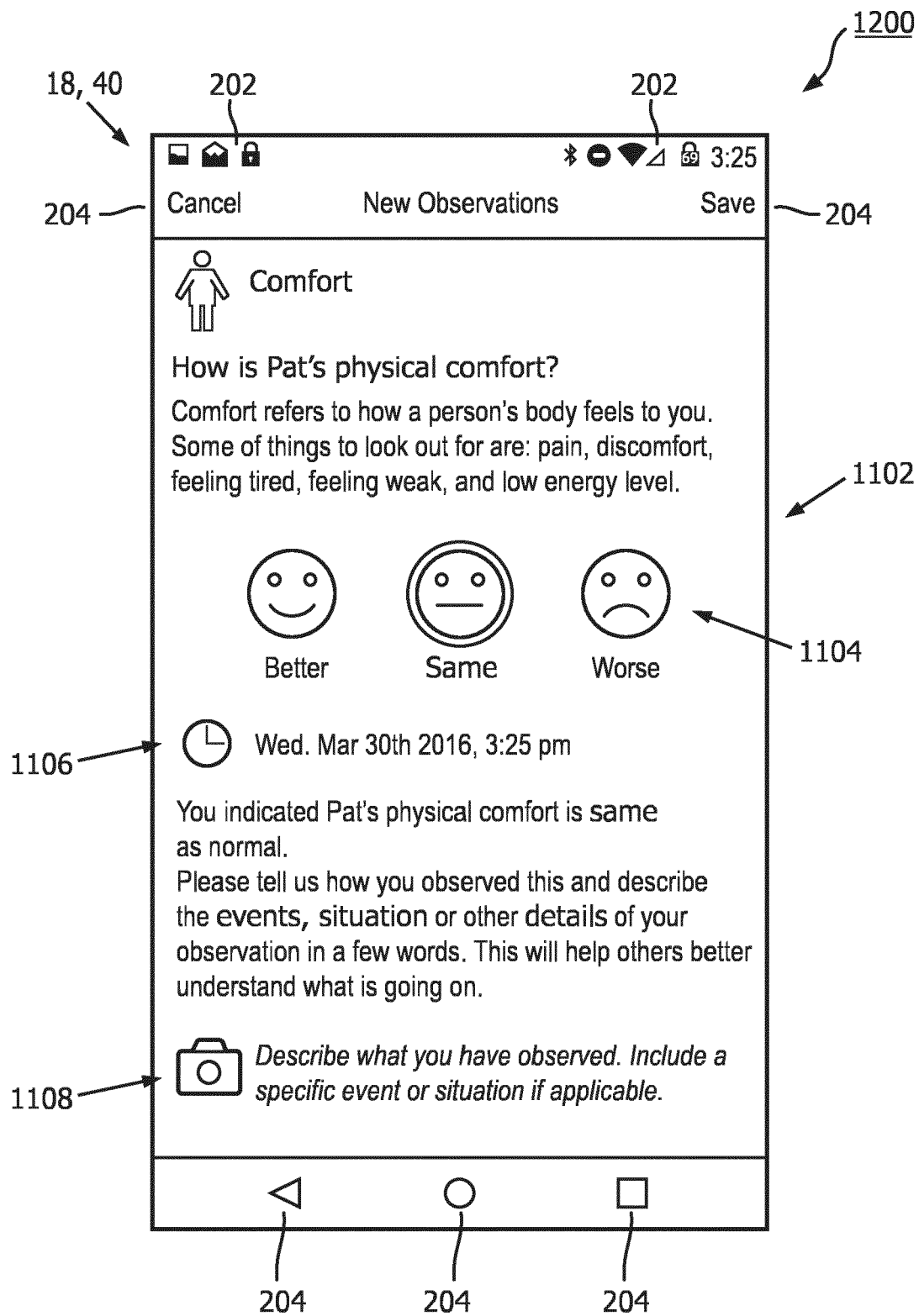
FIG. 12 illustrates a third example of many possible views configured to receive entry and/or selection of information related to the observations by caregivers.

FIG. 11 and FIG. 12 illustrate views 1100 and 1200 of graphical user interface 40 presented on computing device 18. View 1100 (FIG. 11) is similar to view 400 in FIG. 4 (e.g., view 1100 is a second example of many possible views configured to receive entry and/or selection of information related to the observations by caregivers) but presents observation entry and/or selection fields 1102 for a "comfort" observation category. Caregivers may provide a rating via rating field 1104, a date and/or time via date/time field 1106, a description via description field 1108, an image and/or other attachments via description field 1108, and/or other information for a new observation. In FIG. 11, "worse" was selected by a caregiver in rating field 1104. FIG. 12 and view 1200 are similar to FIG. 11 and view 1100 except that, in FIG. 11, "same" was selected by a caregiver in rating field 1104.

Figure 13:
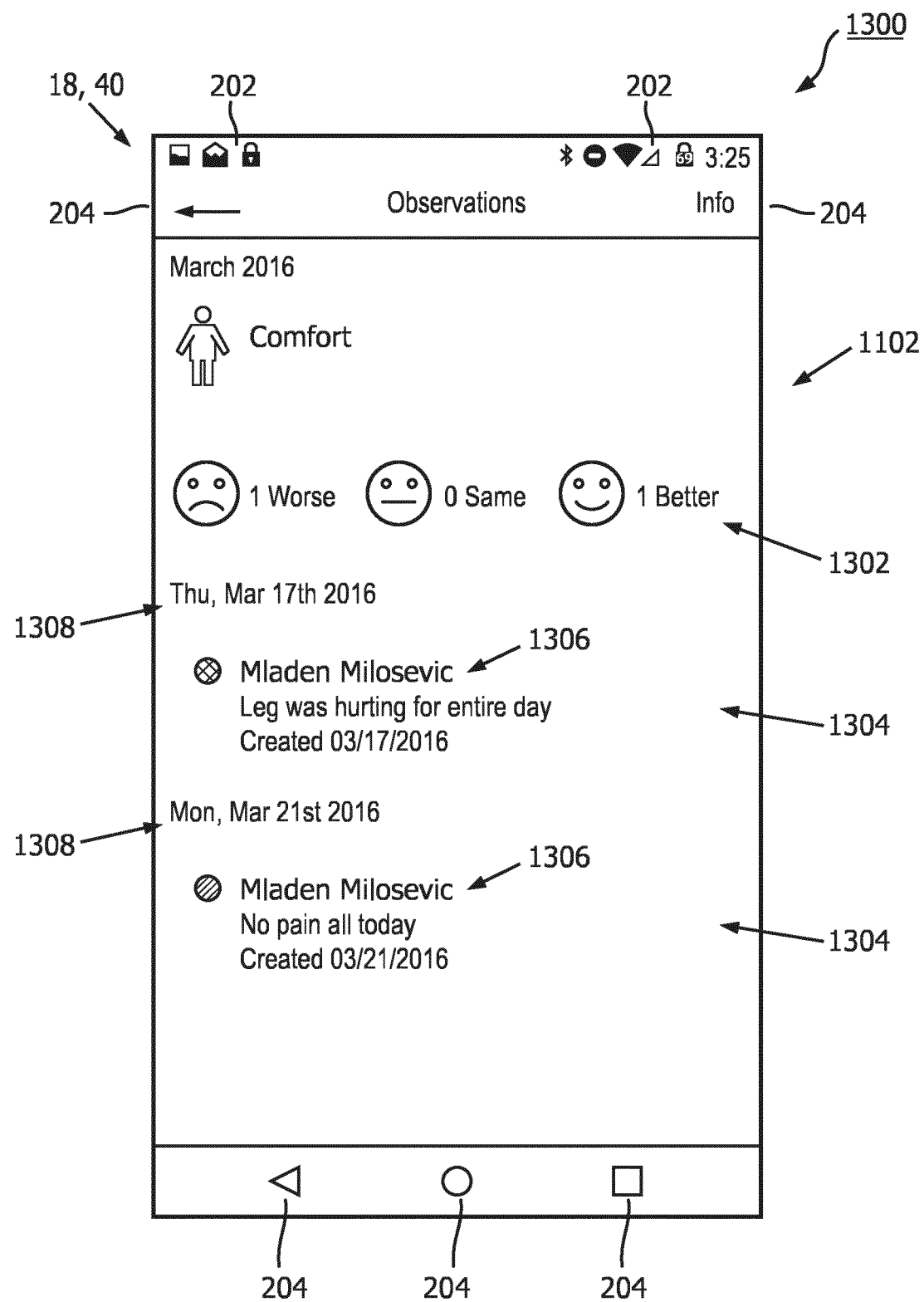
FIG. 13 illustrates another example of a detailed week view of a particular observation category.

FIG. 13 illustrates a view 1300 of graphical user interface 40 similar to view 600 (shown in FIG. 6). View 1300 illustrates a detailed week view of the comfort observation category. A comfort observation count by rating field 1302 is shown along with description fields 1304, author (e.g., caregiver) fields 1306, and rating fields 1308 for two individual observations in that week. View 600 and view 1300 are examples of many possible versions of views that illustrate a detailed week (and/or any other length of time) view of observations from a particular observation category.

Returning to FIG. 1, analysis component 26 is configured to analyze the informal observations, the medical history information, and/or other information. The informal observations, the medical history information, and/or the other information is analyzed to determine one or more of a change and/or a predicted change in the health (e.g., an improvement and/or a decline) of care recipient 12, a medical event experienced by care recipient 12, a predicted medical event that care recipient 12 is more likely to experience, and/or other information. In some embodiments, the medical event experienced by and/or likely to be experienced by care recipient 12 includes one or more of a heart attack, a stroke, a fall, pulmonary exacerbation, and/or other events. In some embodiments, analysis component 26 determines a current and/or predicted health status of care recipient 12. With multiple caregivers providing multiple observations in multiple categories many times, the volume of information produced about the health and/or wellness of care recipient 12 can be large. Recognizing trends, patterns, and/or making correlations between tracked observations of different categories could be difficult for the everyday caregiver, for example. Analysis component 26 is configured to detect and/or predict potential changes in health (e.g., declines and/or increases) based on information conveyed by the observations from the caregivers, the medical history information, and/or other information.

In some embodiments, the analysis includes a pre-processing and feature extraction step using natural language processing (NLP) and image processing techniques configured to facilitate analysis of the textual descriptive notes, the visual images, and/or other observations. Natural language processing techniques are applied to the textual data and image processing techniques are applied to any photos attached to observations, for example. Some NLP techniques that can be applied to the data include sentiment analysis that looks at positive/negative, subjective/objective, or feature/aspect information in the provided text data. When image data is used computer vision techniques to analyze tissue as it is in the healing process. Once an image is taken, a segmentation algorithm is used to extract features from the image. Comparison of images over time will provide information about how the wound, for example is healing.

In some embodiments, the analysis includes determining within category features (e.g., how many "bad" ratings for a particular category), features that cover a combination of categories (e.g., a "bad" overall rating for "happiness" is related to the "bad" overall rating for "body"), and/or other determinations. In some embodiments, analysis component 26 communicates the results of the analysis (e.g., the determination of a change in the health of care recipient 12, a medical event experienced by care recipient 12, and/or other information) to feedback component 28. In some embodiments, the communication includes information related to one or more categories of observations on which the analysis was based.

Feedback component 28 is configured to generate actionable feedback for caregivers. The actionable feedback is generated for the caregivers based on the analysis and/or other information. In some embodiments, feedback component 28 is configured to cause presentation of the actionable feedback to the multiple caregivers on computing devices 18 and/or other computing devices. The actionable feedback is presented to the multiple caregivers via graphical user interface 40 and/or other interfaces. The actionable feedback comprises recommendations for managing the health of care recipient 12, supporting content related to the recommendations, alerts, and/or other information. The recommendations may include suggestions to visit a doctor and/or other medical services provider, suggestions for lifestyle and/or diet changes, suggestions for changing the home environment of care recipient 12 (e.g., place an air filter in the home, keep the home warmer, rearrange the furniture to reduce tripping, etc.), suggestions for visits by caregivers with care recipient 12, suggestions for discussions (e.g., topics for discussion) the caregivers should have with care recipient 12, suggestions for engaging other caregivers to help, and/or other recommendations. The supporting content comprises information related to the recommendations obtained from one or more external sources of data and/or other sources. In some embodiments, the supporting content includes one or more of an article, a video, a website, a news story, a social media post, and/or other supporting content. In some embodiments, the supporting content is obtained from one or more external information sources (e.g., external resources 16) such as medical literature databases (e.g., articles), the Internet (e.g., websites such as blogs etc.), social media sources (e.g., social media posts), news outlets (e.g., news stories), and/or other sources of information. In embodiments, the alerts comprise visual (e.g., color coded) and/or audible alerts communicated via graphical user interface 40 and/or computing devices 18, emails, texts, phone calls, and/or other alerts. In some embodiments, the alerts may be displayed with and/or otherwise incorporated into the actionable feedback. In some embodiments, the alerts may be provided to the caregivers separately from the recommendations and/or the supporting content.

By way of a non-limiting example, the based on observations made during a previous week, analysis component 26 may predict that care recipient 12 is at higher risk for a fall. An alert is provided to the caregivers via feedback component 28. Feedback component 28 pulls an article from an AARP articles database (e.g., included in external resources 16) that provides advice on how to modify the home to be safer for care recipient 12 and also suggests that the caregivers look into personal emergency response systems.

Figure 14:
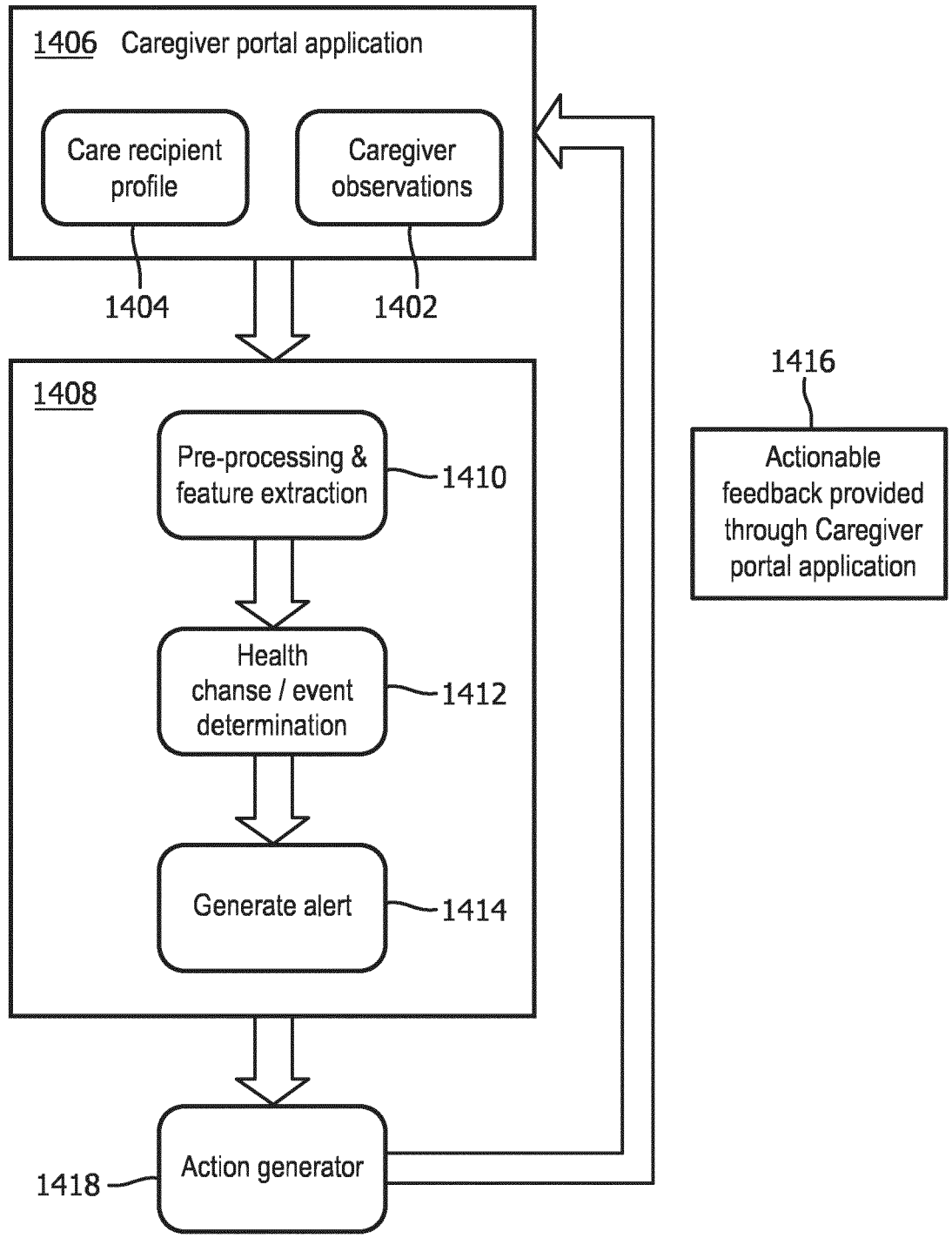
FIG. 14 summarizes operations performed by a processor included in the system.

By way of a second non-limiting example, the operations performed by medical information component 22, interface component 24, analysis component 26, feedback component 28, and/or other components are summarized in FIG. 14. As shown in FIG. 14, caregiver observations 1402 and care recipient profile information 1404 (e.g., including the medical history information is obtained via the caregiver portal application 1406 and/or from other sources of information (e.g., as described above relative to medical information component and interface component 24 shown in FIG. 1). This obtained information is analyzed 1408 (e.g., as described above related to analysis component 26 shown in FIG. 1). The analysis includes pre-processing and feature extraction 1410; determining one or more of a change and/or a predicted change in the health (e.g., an improvement and/or a decline) of care recipient 12 (FIG. 1), a medical event experienced by care recipient 12, a predicted medical event that care recipient 12 is more likely to experience, and/or other information 1412; alert generation 1414; and/or other operations. Responsive to completion of the analysis, actionable feedback 1416 is generated 1418 for caregivers.

Returning to FIG. 1, in some embodiments, report component 30 is configured to generate a summary report. There are times when it may be helpful for the caregivers to share the current and/or predicted health status of care recipient 12, the determination of a change in the health of care recipient 12, a medical event experienced by care recipient 12, and/or other information related to care recipient 12 with healthcare providers and/or other entities. Report component 30 is configured to provide an overview of such information to the caregiver (e.g., a print out, an email, etc.) that can then be shared with a physician, for example. The summary report is generated for a healthcare provider and/or other caregivers based on the actionable feedback, the analysis, the informal observations, and/or other information. For example, a caregiver and/or subject may bring the generated summary report to a doctor's appointment, may communicate (e.g., email) the generated report to a doctor and/or other caregiver treating the subject, etc. In some embodiments, report component 30 is configured such that the caregiver requests the report (e.g., via one or more fields in one or more views of graphical user interface 40) and can decide (e.g., again via entries and/or selections made via one or more fields in one or more views of graphical user interface 40) which items to include in a summary report, a date range for observations the report should summarize, and/or other information to include. For example, in a prior appointment, a doctor may have changed the dosage of a medication taken by care recipient 12, and requested that the caregivers monitor symptoms in caregiver 12 over the next week. In response, the caregivers may create an observation category called "Medication Symptoms" and logs observations over the week. When the follow-up appointment occurs, the caregivers may show the doctor a report of observations made for the medication symptoms category without having to recall this information on the spot in the doctor's office. Advantageously, this increases communication between patient, caregivers and physicians.

Electronic storage 50 comprises electronic storage media that electronically stores information. The electronic storage media of electronic storage 50 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 50 may be (in whole or in part) a separate component within system 10, or electronic storage 50 may be provided (in whole or in part) integrally with one or more other components of system 10 (e.g., computing devices 18, processor 20, etc.). In some embodiments, electronic storage 50 may be located in a server together with processor 20, in a server that is part of external resources 16, in a computing device 18 associated with a caregiver and/or other users, and/or in other locations. Electronic storage 50 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 50 may store software algorithms, information determined by processor 20, information received via a computing device 18 and/or graphical user interface 40 and/or other external computing systems, information received from external resources 16, information received from sensors 14, and/or other information that enables system 10 to function as described herein. By way of a non-limiting example, electronic storage 50 may store information related to the observations made by the caregivers and/or other information.

Figure 15:
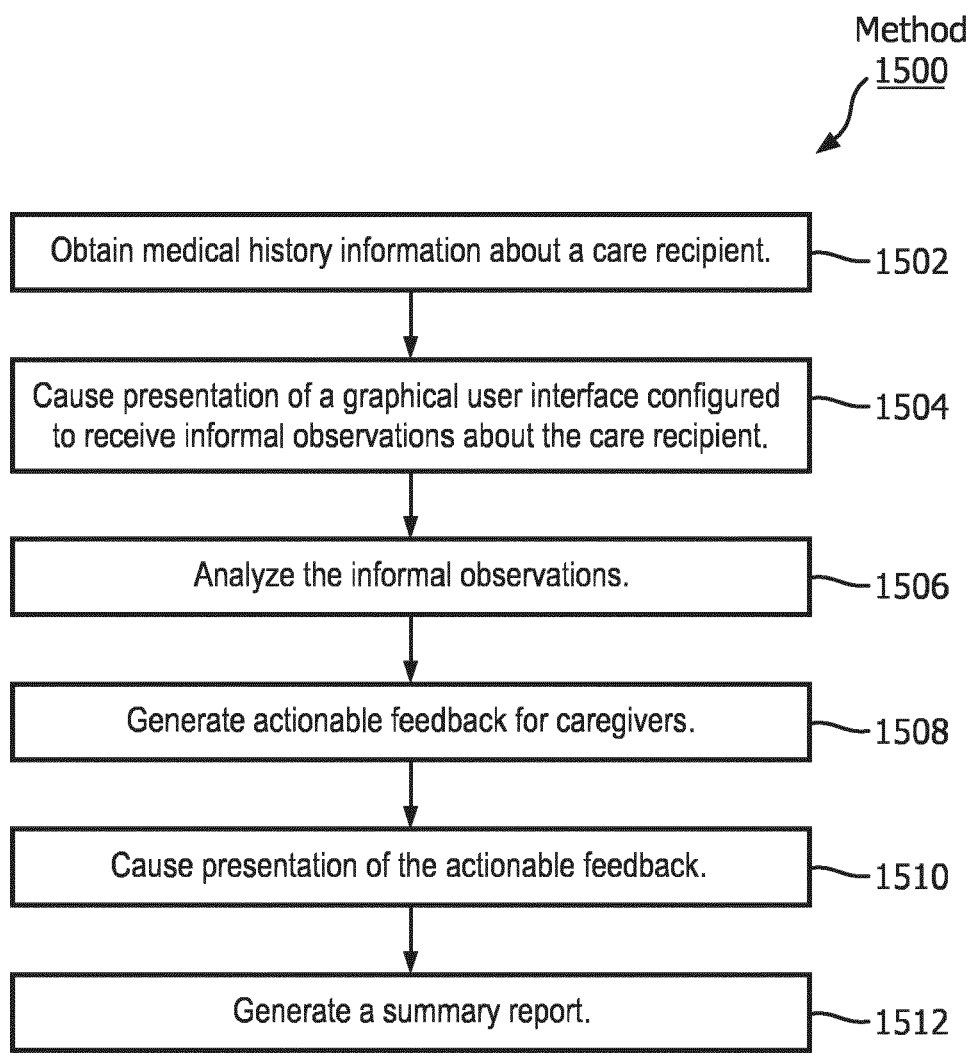
FIG. 15 illustrates a method for tracking informal observations by multiple caregivers about a care recipient and providing actionable feedback to the multiple caregivers for managing health of the care recipient based on the informal observations with an observation system.

FIG. 15 illustrates a method 1500 for tracking informal observations by multiple caregivers about a care recipient and providing actionable feedback to the multiple caregivers for managing health of the care recipient based on the informal observations with an observation system. The system comprises one or more hardware processors and/or other components. The one or more hardware processors are configured by machine readable instructions to execute computer program components. The computer program components include a medical information component, an interface component, an analysis component, a feedback component, a report component, and/or other components. The operations of method 1500 presented below are intended to be illustrative. In some embodiments, method 1500 may be accomplished with one or more additional operations not described, and/or without one or more of the operations discussed. Additionally, the order in which the operations of method 1500 are illustrated in FIG. 15 and described below is not intended to be limiting.

In some embodiments, method 1500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1500 in response to instructions stored electronically on an electronic storage medium. The one or more processing devices may include one or more devices configured through hardware, firmware, and/or software to be specifically designed for execution of one or more of the operations of method 1500.

At an operation 1502, medical history information about the care recipient is obtained. The medical history information indicates the health of the care recipient including one or more medical conditions experienced by the care recipient and/or other medical history information. In some embodiments, the medical history information is obtained from one or more external databases (e.g., a medical records database associated with a health care provider, electronic storage included in system 10 (e.g., electronic storage 50 shown in FIG. 1), one or more sensors (e.g., sensors 14) configured to generate output signals that convey information related to the heath of the care recipient, and/or other sources of the medical history information. In some embodiments, operation 1502 is performed by a processor component the same as or similar to medical information component 22 (shown in FIG. 1 and described herein).

At an operation 1504, presentation of a graphical user interface is caused. The graphical user interface is configured to receive informal observations about the care recipient. In some embodiments, the observations include one or more of textual descriptive notes, ratings, dates of the observations, visual images related to the observations, and/or other observations. The graphical user interface is configured to facilitate entry and/or selection of the informal observations by the multiple caregivers. The graphical user interface is presented on individual computing devices associated with individual caregivers. The graphical user interface comprises one or more views corresponding to one or more observation categories, and one or more fields within an individual view corresponding to textual descriptive notes, ratings, dates, visual images, and/or other observations. In some embodiments, responsive to the entry and/or selection of the observations, one or more follow up questions based on the observations are presented via the graphical user interface. In some embodiments, operation 1504 is performed by a processor component the same as or similar to interface component 24 (shown in FIG. 1 and described herein).

At an operation 1506, the informal observations, the medical history, and/or other information is analyzed. The informal observations, the medical history information, and/or the other information is analyzed to determine one or more of a change in the health of the care recipient, a medical event experienced by the care recipient, and/or other information. In some embodiments, the medical event experienced by the care recipient includes one or more of a heart attack, a stroke, a fall, and/or other events. The analysis includes a pre-processing and feature extraction step using natural language processing and image processing techniques configured to facilitate analysis of the textual descriptive notes, the visual images, and/or other observations. In some embodiments, operation 1506 is performed by a processor component the same as or similar to analysis component 26 (shown in FIG. 1 and described herein).

At an operation 1508, actionable feedback is generated for caregivers. The actionable feedback is generated for the multiple caregivers based on the analysis. The actionable feedback comprises recommendations for managing the health of the care recipient, supporting content related to the recommendations, and/or other information. The supporting content comprises information related to the recommendations obtained from one or more external sources of data and/or other sources. In some embodiments, the supporting content includes one or more of an article, a video, a website, and/or other supporting content. In some embodiments, operation 1508 is performed by a processor component the same as or similar to feedback component 28 (shown in FIG. 1 and described herein).

At an operation 1510, presentation of the actionable feedback is caused. The actionable feedback is presented to the multiple caregivers via the graphical user interface. In some embodiments, operation 1510 is performed by a processor component the same as or similar to feedback component 28 (shown in FIG. 1 and described herein).

At an operation 1512, a summary report is generated. The summary report is generated for a healthcare provider based on the actionable feedback, the analysis, the informal observations, and/or other information. For example, a caregiver and/or subject may bring the summary report to a doctor's appointment, may communicate (e.g., email) the report to a doctor and/or other caregiver treating the subject, etc. In some embodiments, operation 1512 is performed by a processor component the same as or similar to report component 30 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to track informal observations by multiple caregivers about a care recipient and provide actionable feedback to the multiple caregivers for managing health of the care recipient based on the informal observations, the system comprising one or more hardware processors configured by machine readable instructions to:
    obtain medical history information about the care recipient, the medical history information indicating the health of the care recipient including one or more medical conditions experienced by the care recipient;
    cause presentation of a graphical user interface configured to facilitate selection of one or more selectable observation categories for entry of the informal observations by each of the multiple caregivers, the graphical user interface presented on individual computing devices associated with individual caregivers, wherein the one or more selectable categories are customizable, such that at least one of the one or more selectable observation categories can be removed and a new selectable observation category can be added to the one or more selectable observation categories;
    process the informal observations using a natural language processing sentiment analysis to categorize each informal observation as at least one of: positive, negative, subjective, objective, feature-related, and aspect-related;
    analyze the processed informal observations and the medical history information by determining a trend among the processed informal observations and the medical history to identify one or more of a change in the health of the care recipient or a medical event experienced by the care recipient;
    generate actionable feedback for at least one of the multiple caregivers based on the analysis, the actionable feedback comprising recommendations for managing the health of the care recipient and supporting content related to the recommendations, the supporting content comprising information related to the recommendations obtained from one or more external sources of data; and
    cause presentation of the actionable feedback to the at least one of the multiple caregivers via the graphical user interface, wherein the actionable feedback is configured to assist the at least one of the multiple caregivers in obtaining medical services for the care recipient such that treatment is provided to the care recipient.

2. The system of claim 1, wherein the one or more hardware processors are further configured to generate a summary report for a healthcare provider based on the actionable feedback, the analysis, and the informal observations.

3. The system of claim 1, wherein the one or more hardware processors are configured such that the informal observations include one or more of textual descriptive notes, ratings, dates of the observations, or visual images related to the informal observations.

4. The system of claim 3, wherein the one or more hardware processors are further configured such that processing further comprises image processing techniques configured to facilitate analysis of the visual images.

5. The system of claim 1, wherein the one or more hardware processors are configured such that the graphical user interface comprises one or more views corresponding to the one or more observation categories, and one or more fields within an individual view of the one or more views corresponding to textual descriptive notes, ratings, dates, and/or visual images.

6. The system of claim 1, further comprising one or more sensors configured to generate output signals that convey information related to the heath of the care recipient, wherein the one or more hardware processors are configured such that the information in the output signals is included in the obtained medical history information.

7. A method for tracking informal observations by multiple caregivers about a care recipient and providing actionable feedback to the multiple caregivers for managing health of the care recipient based on the informal observations with an observation system, the system comprising one or more hardware processors, the method comprising:
    obtaining medical history information about the care recipient, the medical history information indicating the health of the care recipient including one or more medical conditions experienced by the care recipient;
    causing presentation of a graphical user interface configured to facilitate selection of one or more selectable observation categories for entry of the informal observations by each of the multiple caregivers, the graphical user interface presented on individual computing devices associated with individual caregivers, wherein the one or more selectable categories are customizable, such that at least one of the one or more selectable observation categories can be removed and a new selectable observation category can be added to the one or more selectable observation categories;
    processing the informal observations using a natural language processing sentiment analysis to categorize each informal observation as at least one of: positive, negative, subjective, objective, feature-related, and aspect-related;
    analyzing the informal observations and the medical history information by determining a trend among the processed informal observations and the medical history to identify one or more of a change in the health of the care recipient or a medical event experienced by the care recipient;
    generating actionable feedback for at least one of the multiple caregivers via a caregiver device associated with the at least one of the multiple caregivers, wherein the actionable feedback is based on the analysis, the actionable feedback comprising recommendations for managing the health of the care recipient and supporting content related to the recommendations, the supporting content comprising information related to the recommendations obtained from one or more external sources of data;

causing presentation of the actionable feedback to the caregiver device associated with the at least one of the multiple caregivers via the graphical user interface, wherein the actionable feedback is configured to assist the at least one of the multiple caregivers in obtaining medical services for the care recipient such that treatment is provided to the care recipient.

8. The method of claim 7, further comprising generating a summary report for a healthcare provider based on the actionable feedback, the analysis, and the informal observations.

9. The method of claim 7, wherein the informal observations include one or more of textual descriptive notes, ratings, dates of the observations, or visual images related to the informal observations.

10. The method of claim 9, wherein the processing further comprises image processing techniques configured to facilitate analysis of the visual images.

11. The method of claim 7, wherein the graphical user interface comprises one or more views corresponding to the one or more observation categories, and one or more fields within an individual view of the one or more views corresponding to textual descriptive notes, ratings, dates, and/or visual images.

12. The method of claim 7, further comprising generating output signals that convey information related to the heath of the care recipient, wherein the information in the output signals is included in the obtained medical history information.

13. The system of claim 1, wherein the one or more hardware processors are further configured to:
    determine a presence of one or more informal observations of first and second selectable observation categories of the one or more selectable observation categories during a period of time, each of the one or more informal observations of the first and second selectable observation categories comprising an associated rating that is at least one of positive, neutral, or negative; and
    automatically display an indicator on the graphical user interface, the indicator representing the presence of the one or more informal observations of the first and second selectable observation categories during the period of time, and a characteristic of the indicator on the graphical user interface, the characteristic representing a most negative rating associated with the one or more informal observations of the first and second selectable observation categories during the period of time.

14. The method of claim 7, further comprising the steps of:
    determining a presence of one or more informal observations of first and second selectable observation categories of the one or more selectable observation categories during a period of time, each of the one or more informal observations of the first and second selectable observation categories comprising an associated rating that is at least one of positive, neutral, or negative; and
    automatically displaying an indicator on the graphical user interface, the indicator representing the presence of the one or more informal observations of the first and second selectable observation categories during the period of time, and a characteristic of the indicator on the graphical user interface, the characteristic representing a most negative rating associated with the one or more informal observations of the first and second selectable observation categories during the period of time.

* * * * *